US012648869B2

(12) United States Patent
Hewes

(10) Patent No.: US 12,648,869 B2
(45) Date of Patent: Jun. 9, 2026

(54) ARM BRACE WITH ADJUSTABLE PERMITTED FLEXION

(71) Applicant: Infusion Guardian LLC, Kailua, HI (US)

(72) Inventor: Casey James Hewes, Vernon (CA)

(73) Assignee: Infusion Guardian LLC, Honolulu, HI (US)

( * ) Notice: Subject to any disclaimer, the term of this patent is extended or adjusted under 35 U.S.C. 154(b) by 289 days.

(21) Appl. No.: 18/334,156

(22) Filed: Jun. 13, 2023

(65) Prior Publication Data

US 2024/0415686 A1 Dec. 19, 2024

(51) Int. Cl.
*A61F 5/01* (2006.01)

(52) U.S. Cl.
CPC ...... *A61F 5/013* (2013.01); *A61F 2005/0137* (2013.01); *A61F 2005/0167* (2013.01)

(58) Field of Classification Search
CPC .... A61F 5/0106; A61F 5/0118; A61F 5/0123; A61F 5/013; A61F 5/373; A61F 5/05841; A61F 5/0585; A61F 5/05858; A61F 5/05866; A61F 13/10; A61F 2005/0137; A61F 2005/0167; A61H 1/0237; A61H 1/0277; A61H 1/0285; A41D 19/01582; A41D 19/01588
See application file for complete search history.

(56) References Cited

U.S. PATENT DOCUMENTS

| | | | | |
|---|---|---|---|---|
| 4,856,501 A * | 8/1989 | Castillo | ................. | A61F 5/0123 602/16 |
| 5,792,086 A * | 8/1998 | Bleau | ................... | A61F 5/0123 602/26 |
| 5,814,000 A * | 9/1998 | Kilbey | ................. | A61F 5/0125 602/26 |
| 7,182,088 B2 | 2/2007 | Jenkins | | |
| 2018/0296380 A1* | 10/2018 | Wang | ................... | A61F 5/0125 |

* cited by examiner

*Primary Examiner* — Alireza Nia

*Assistant Examiner* — Andrew Jun-Wai Mok

(74) *Attorney, Agent, or Firm* — Timothy G. Ackermann

(57) ABSTRACT

An arm brace providing adjustable permitted flexion of the arm at the elbow includes an adjustable upper arm section, an adjustable lower arm section, a stoppable hinge connecting the arm sections, a stop to stop the hinge, and adjustable closures to connect the brace system to the upper and lower arm of a patient around the elbow. The stoppable hinge includes a stop receiver with slot detents for inserting a stopping tab at angular settings for permitted arm flexion, and an edge, for interacting with the stopping tab. The upper and lower arm sections are adjustable left-to-right to fit the patient's arm by a ratchet mechanism.

24 Claims, 10 Drawing Sheets

ARM BRACE WITH ADJUSTABLE PERMITTED FLEXION

BACKGROUND OF THE INVENTION

The present invention solves a problem with protecting an intravenous injection (IV) placement in the antecubital (AC) elbow of a patient. Many patients bend their elbows subconsciously and are unable to control this motor movement. If a patient with an IV with an AC elbow placement bends (flexes) the elbow too far, the IV can be pinched, slowing or interrupting flow of the liquid therein. This can prolong the time needed for the IV. This can also blockage, occlusion, or obstruction at an AC elbow intravenous site, which are all potentially dangerous. Also dangerous is the possibility of infiltration of the liquid into surrounding tissues due to such problems. In addition, undesirable excess flexion of the elbow can damage tissues (including the vein and/or injection site) by bending the tissue around the injection needle or other structure used for the IV.

As a result of such potential dangers, alarm systems may be used to warn medical personnel if an IV is unintentionally disturbed. Disturbing the IV then sets off an alarm. But a vast majority of such alarms are false. This can lead to alarm fatigue for medical personnel, who must respond to the alarm nonetheless, because ignoring a clinically actionable alarm can prove deadly. Alarm fatigue is a patient safety risk because medical personnel can become desensitized to safety alerts/alarms and can thus ignore or fail to respond appropriately to such warnings.

Completely immobilizing the patient's elbow, however, may not be desirable. Thus, it is desirable to permit desirable or permissible arm flexion at the elbow (or elbow flexion), while preventing undesirable or impermissible arm flexion. This can reduce false alarms by permitting alarms to only alert upon the impermissible arm flexion, which should be prevented by the brace system, or to omit alarms entirely due to the protection of the brace system.

Accordingly, the present invention is attached at the elbow of a patient having an IV at an IV site, and permits desirable arm flexion at the elbow, up to a stopping point, but prevents undesirable arm flexion.

BRIEF STATEMENT OF THE INVENTION

In an embodiment, a brace system includes an upper arm section, a lower arm section, a stoppable hinge connecting the arm sections, a stop to stop the hinge, and closures to connect the brace system to the upper and lower arm of a patient around the elbow.

In an embodiment, a brace system includes an adjustable upper arm section, an adjustable lower arm section, a stoppable hinge connecting the arm sections, a stop to stop the hinge, and adjustable closures to connect the brace system to the upper and lower arm of a patient around the elbow.

In an embodiment, a brace system includes an upper brace with a stoppable hinge section and supporting arms, a lower brace, with a stoppable hinge section and supporting arms, a connector connecting the stoppable hinge sections, and adjustable straps. In an embodiment, the upper brace and the lower brace each includes a left and a right brace, each of the left and right braces including proximal arms and distal arms. In an embodiment, the arms include side portions for extending toward the bottom of the patient's arm, and connection portions for connecting an arm on one side brace (left/right) to an arm on the opposing (right/left) side brace.

In an embodiment, the spacing between the side braces of the upper brace and of the lower brace are adjustable between the connection portions of the side braces via ratchet mechanisms, which ratchets as distance is reduced, but may be released by flexing one or more of the connection portions. In an embodiment, the arms have a flexed position and an unflexed position. In an embodiment, the flexed position permits releasing the ratchet mechanisms to allow increasing the spacing between the side braces of the upper brace and of the lower brace, and the unflexed position allows the ratchet mechanisms to holding the arms in in a locked position that allows decreasing the spacing between the side braces of the upper brace and of the lower brace while preventing that spacing from increasing without departing the locked position and the unflexed position. In an embodiment, the left and right braces of the upper brace and lower brace each include a rail with closure attachment points, and a connection section with a connecting hole for the connector. In an embodiment, a connection portion on a side brace includes a proximal and a distal arm extending from a rail, a crosspiece spaced from the rail and connecting the arms transversely, and receiving slots formed in the arms for a mating arm. In an embodiment, the receiving slots each include an internal flat wall longitudinal to the arm, an opposing toothed wall formed of meshing teeth, and a mouth on each arm exposing the receiving slots. In an embodiment, a connection portion on a side brace includes a proximal and a distal arm extending from a rail with a flexible piece spaced from the rail, and a locking ends with teeth located distally on the arms. In an embodiment, the stoppable hinge sections include a stop receiver with angular settings for permitted arm flexion. In embodiment, the stop receiver includes multiple stop detents separated by angular spacing, and the angular settings include at least a least flexion setting, an intermediate flexion setting, and a most flexion setting. In an embodiment, the stoppable hinge sections include an edge, for interacting with a stop, and an edge spacing between the edge and the connector. In an embodiment, the stop includes a stopping tab including a slot end and opposing tab end, and a slot for interacting with a stop detent.

In an embodiment, a method of protecting an elbow IV site by preventing impermissible elbow flexion, includes fitting an upper arm section to a patient's upper arm, fitting a lower arm section to a patient's lower arm, where the arm sections are connected by a stoppable hinge, and inserting a stop in the stoppable hinge.

In an embodiment, a method of preventing impermissible elbow flexion includes fitting an upper arm section to a patient's upper arm, fitting a lower arm section to a patient's lower arm, where the arm sections are connected by a stoppable hinge, and inserting a stop in the stoppable hinge.

In an embodiment, the stoppable hinge includes angular settings for permitted elbow flexion and includes the step of inserting the stop at a selecting angular setting.

In an embodiment, a method of preventing impermissible elbow flexion includes fitting an upper arm section to a patient's upper arm, fitting a lower arm section to a patient's lower arm, where the arm sections are connected by a stoppable hinge, inserting a pair of stops in the stoppable hinge, and closing closures around the upper and lower arms to connect the brace system to the upper and lower arm of a patient around the elbow.

In an embodiment, a method of preventing impermissible elbow flexion includes fitting an upper arm section to a patient's upper arm, fitting a lower arm section to a patient's lower arm, where the arm sections are connected by a stoppable hinge, inserting a pair of stops in the stoppable hinge at a first angular setting, removing the stops from the stoppable hinge, and inserting a pair of stops in the stoppable hinge at a second, different, angular setting In an embodiment, a method of protecting an elbow IV site includes fitting an upper arm section to a patient's upper arm, fitting a lower arm section to a patient's lower arm, where the arm sections are connected by a stoppable hinge, and inserting a stop in the stoppable hinge to form a rotational stop for elbow flexion, and allowing permissible elbow flexion up to the rotational stop. In an embodiment, a method of protecting an elbow IV site includes fitting an upper arm section to a patient's upper arm, fitting a lower arm section to a patient's lower arm, where the arm sections are connected by a stoppable hinge, and inserting a stop in the stoppable hinge to form a rotational stop for elbow flexion, allowing permissible elbow flexion up to the rotational stop, and preventing impermissible elbow flexion past the rotational stop. In an embodiment, forming a rotational stop includes the step of inserting the stop at a selected angular setting.

In an embodiment, a method of reducing false alarms in an alarm system for monitoring an elbow IV site includes inserting a stop at a selected angular setting in a stoppable hinge to form a rotational stop for elbow flexion, where the stoppable hinge connects an upper arm section to a lower arm section, then allowing permissible elbow flexion up to a rotational stop and preventing impermissible elbow flexion past the rotational stop. In embodiment, the method also includes fitting the lower arm section to a patient's lower arm and fitting the upper arm section to a patient's upper arm.

DETAILED DESCRIPTION OF THE INVENTION

Figure 1A:
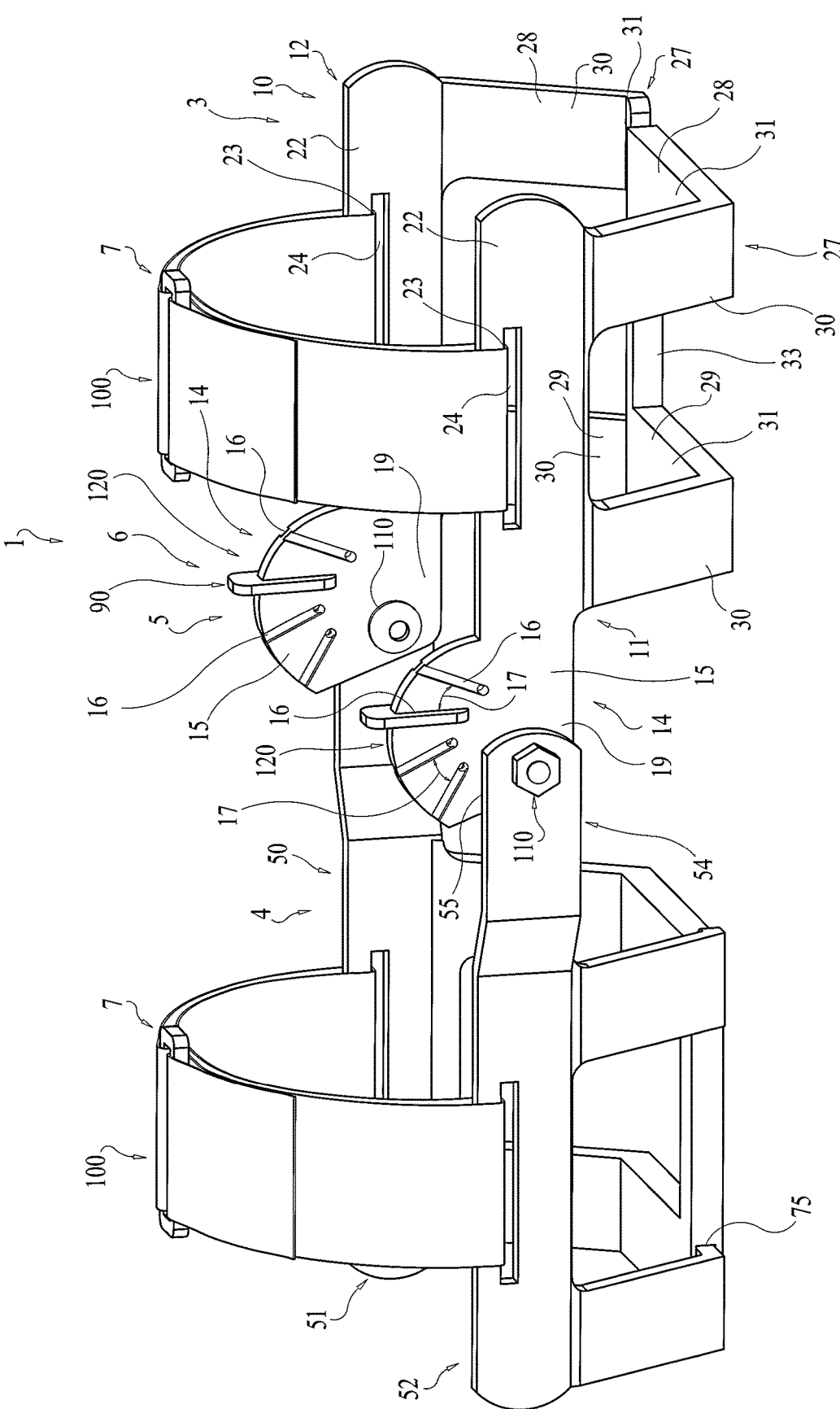
FIGS. 1A & 1B show top, left, proximal views of an embodiment of the present invention in a first and second configuration.
Figure 1B:
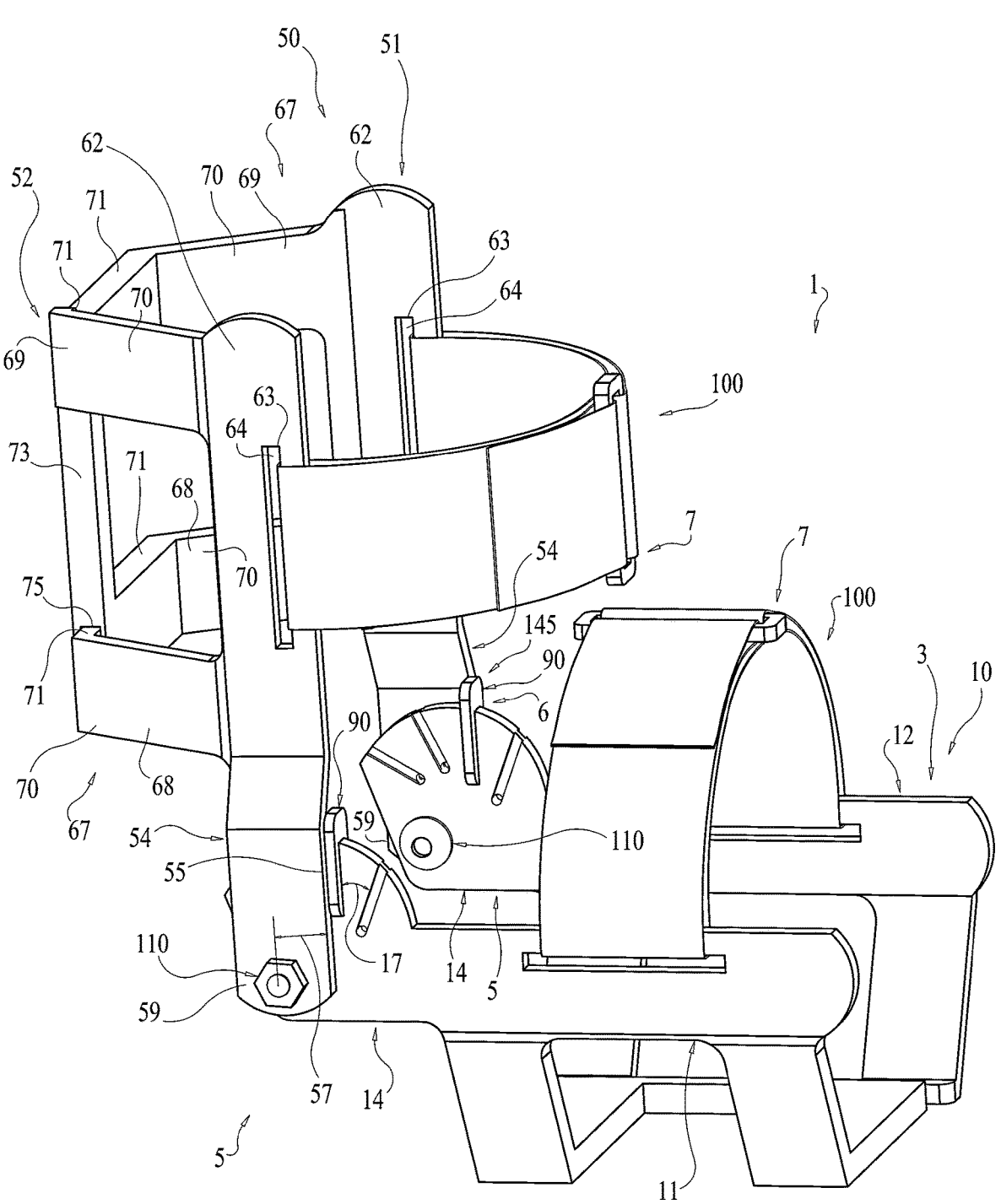
Figure 2:
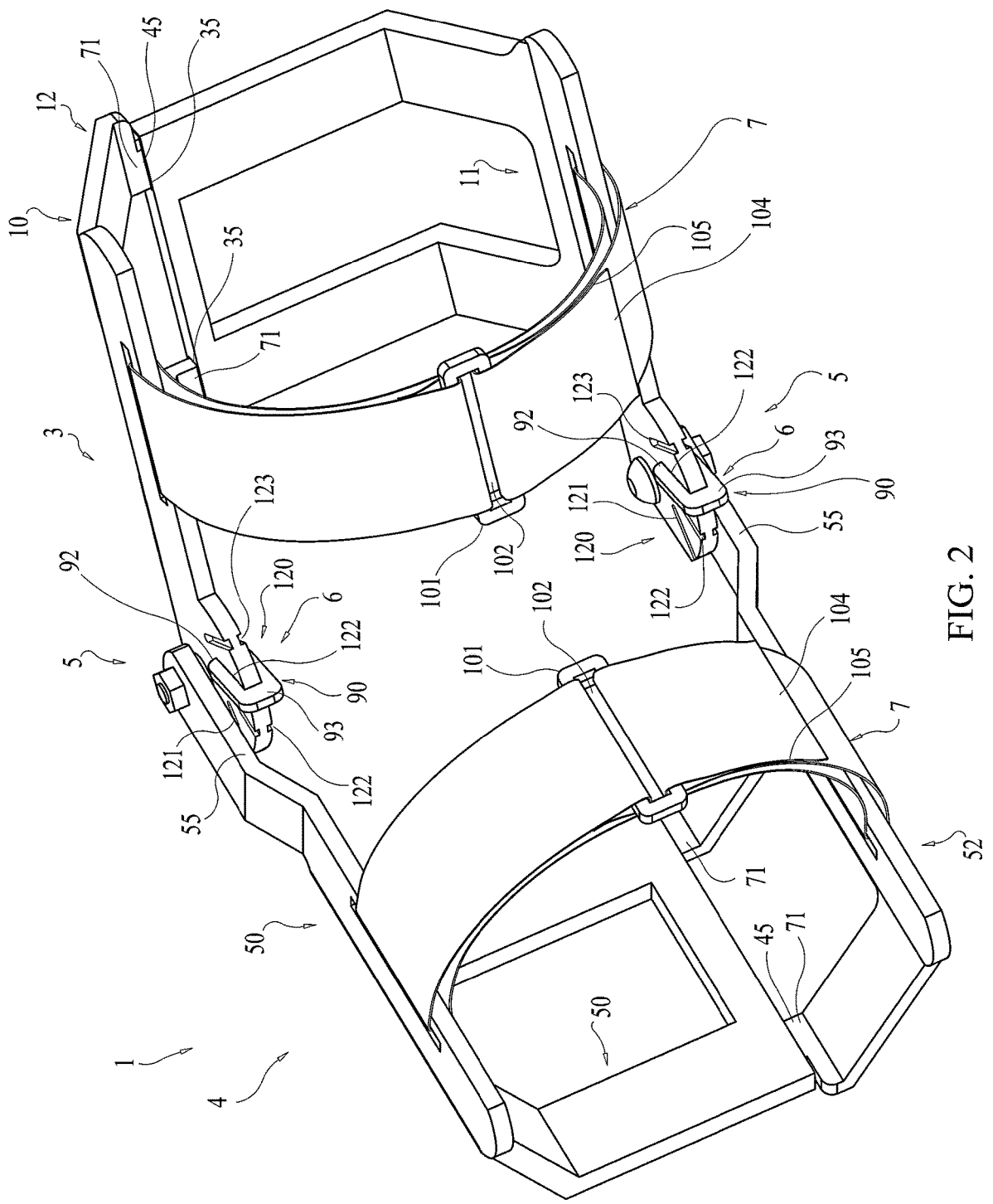
FIG. 2 shows a top, right, proximal view of the embodiment of FIGS. 1A & 1B in a configuration intermediate therebetween.

For a first embodiment, we refer to FIGS. 1A, 1B, 2, and 5A, & 5B.

In a first embodiment, brace system 1 includes adjustable upper arm section 3, adjustable lower arm section 4, stoppable hinge 5 connecting adjustable arm sections 3, 4, stop 6 to stop stoppable hinge 5, and adjustable closures 7 to connect brace system 1 to upper arm 132 and lower arm 133 of patient 130 around elbow 134. In practice, upper arm section 3 and lower arm section 4 are interchangeable, in that the brace system 1 could be reversed to place lower arm section 4 on upper arm 132 and upper arm section 3 on lower arm 133. Adjustable upper arm section 3 may comprise upper brace 10, adjustable lower arm section 4 may include lower brace 50, stoppable hinge 5 may include stoppable hinge section 14 and stoppable hinge section 54 and connector 110, stop 6 may include stopping tab 90, and adjustable closures 7 may include adjustable straps 100. Stop 6 may be inserted into stoppable hinge 5 to form positive rotational stop 141 to control the amount of flexion permitted at elbow 134, thus permitting permissible elbow flexion 142 and preventing impermissible elbow flexion 143. Stoppable hinge 5 permits different placement of stop 6 to adjust permissible elbow flexion 142.

For a second embodiment, we refer generally to the Figs.

In a second embodiment, brace system 1 includes upper brace 10 with stoppable hinge section 14 and supporting arms 27, lower brace 50, with stoppable hinge section 54 and supporting arms 67, connector 110 connecting stoppable hinge sections 14 & 54, and adjustable straps 100.

Upper brace 10 includes left brace 11 and right brace 12, with each of left and right braces 11, 12 including a supporting arm 27. Each supporting arm 27 itself includes proximal arm 28 and distal arm 29. Supporting arms 27 include side portions 30 for extending toward the bottom of the arm of patient 130, and connection portions 31 for connecting an arm on one side brace (left brace 11/right brace 12) to an arm on the opposing side brace (right brace 12/left brace 11). Side portions 30 and connection portions 31 are part of proximal arm 28 and distal arm 29.

Figure 3:
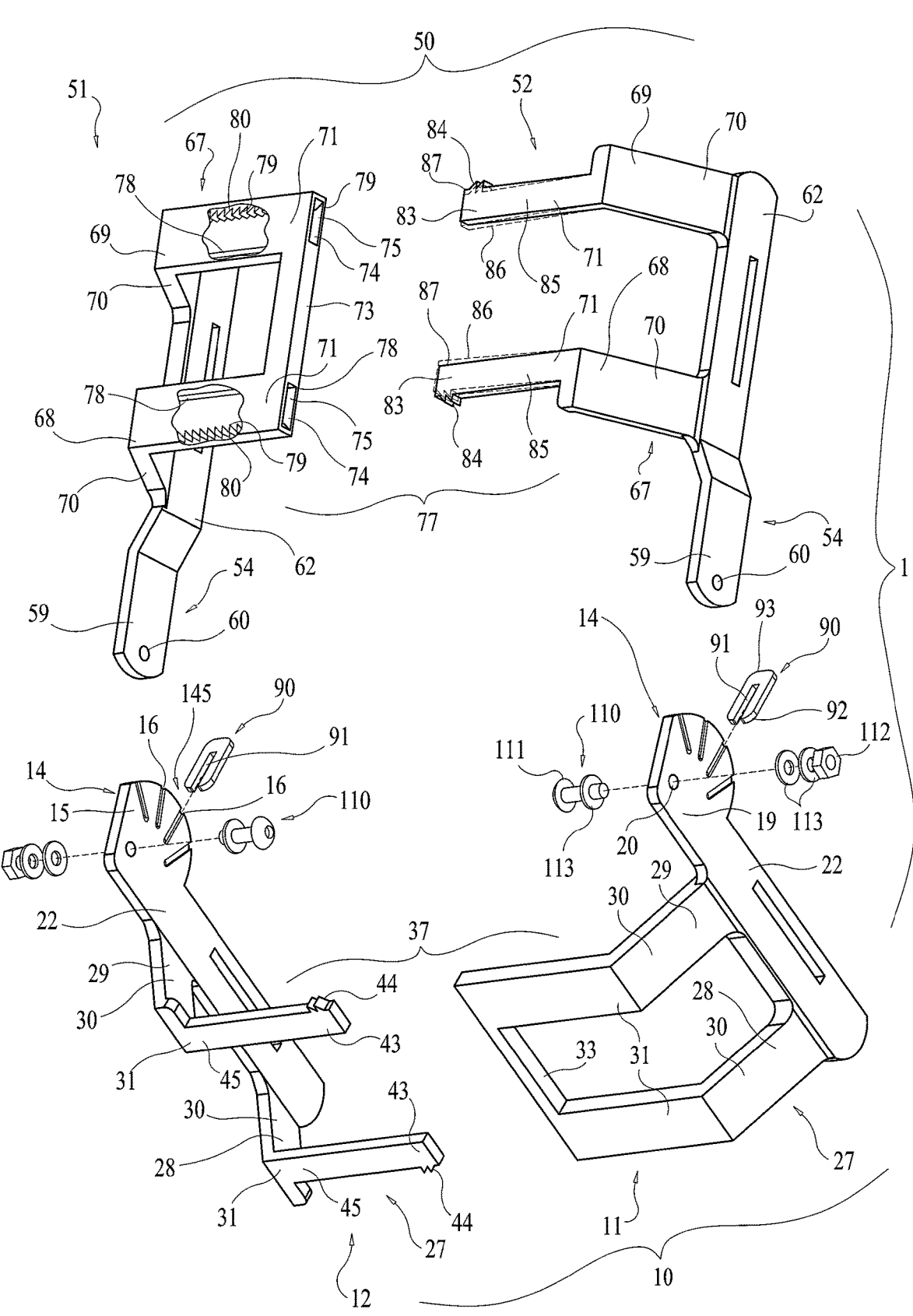
FIG. 3 shows a bottom, left, distal exploded and partial cutaway view of a part of an embodiment of the present invention.
Figure 4A:
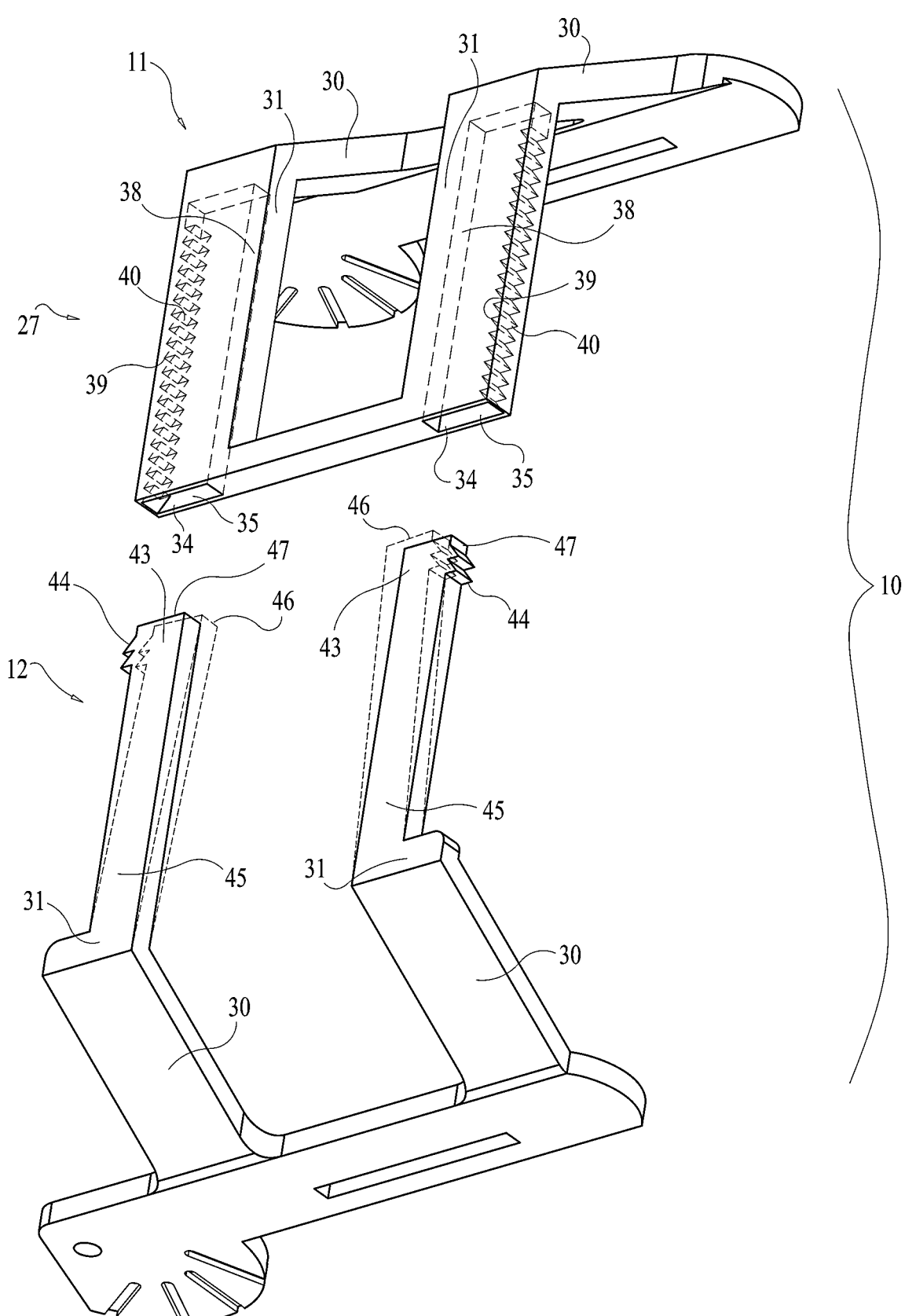
FIGS. 4A & 4B show bottom, right, proximal views of a part of an embodiment of the present invention in a first and second configuration.
Figure 4B:
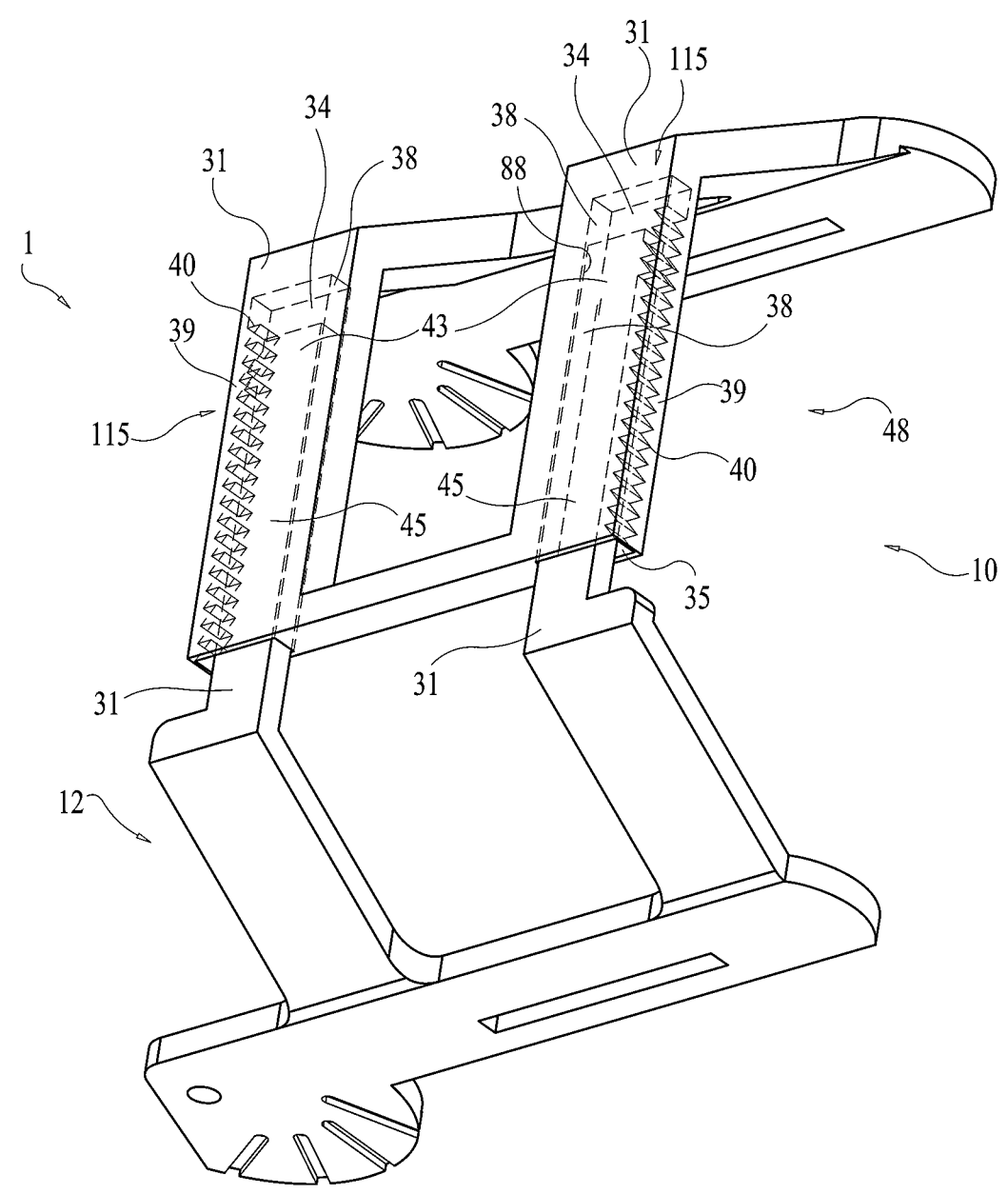

With particular reference to FIGS. 3, 4A, & 4B, on one of left brace 11/right brace 12, connection portion 31 includes proximal arm 28 and distal arm 29 extending from rail 22, crosspiece 33 spaced from rail 22 and connecting proximal arm 28 and distal arm 29 transversely, and receiving slots 34 having mouths 35 formed in proximal arm 28 and distal arm 29 for opposed mating arms on the other of left brace 11/right brace 12. Mouths 35 permit access to receiving slots 34 within each of proximal arm 28 and distal arm 29 by space between flat wall 38 and toothed wall 39 having meshing teeth 40. Toothed walls 39 (and flat walls 38) are in opposing directions in proximal arm 28 and distal arm 29 and are both outboard to permit a compressed flexed position 46 to remove ratchet mechanism 37 from the locked position. Receiving slots 34 each include internal flat wall 38 longitudinal to the arm, opposing toothed wall 39 formed of meshing teeth 40, and mouth 35 on each arm exposing receiving slots 34. On the other of left brace 11/right brace 12, connection portion 31 includes proximal arm 28 and distal arm 29 extending from rail 22, each with flexible piece 45 having locking ends 43 (having teeth 44) facing opposing directions and outboard to permit a compressed flexed position 46 to remove ratchet mechanism 37 from locked position 48 or to back it off (i.e. loosen left brace 11/right brace 12). Flexible pieces 45 are spaced from rail 22 and include locking ends 43 with teeth 44 located distally on the arms. The spacing between side braces (left brace 11/right brace 12) of upper brace 10 are adjustable between connection portions 31 via ratchet mechanisms 37, which ratchets as distance is reduced (i.e. tightening brace 11/right brace 12), but may be released or loosened by flexing one or more of flexible pieces 45. Thus, connection portions 31 are matable to one another to adjustably connect side braces (left brace 11/right brace 12). Supporting arms 27 have flexed position 46 and unflexed position 47, the latter causing the arms to be in locked position 48 with teeth 44 and meshing teeth 40 engaged. Flexed position 46 permits releasing ratchet mechanisms 37 formed by locking ends 43 and toothed walls 39 to allow increasing the spacing between left brace 11 and right brace 12 of upper brace 10

(i.e. loosen brace 11/right brace 12) by disengaging teeth 44 and meshing teeth 40. Unflexed position 47 engages ratchet mechanisms 37 formed by locking ends 43 and toothed walls 39 to allow decreasing the spacing between left brace 11 and right brace 12 (i.e. tighten brace 11/right brace 12) while preventing that spacing from increasing without departing unflexed position 47 and locked position 48; thus teeth 44 and meshing teeth 40 are engaged but permit decreasing spacing.

With particular reference to FIGS. 1A, 2B, 2, 3, & 5A, left brace 11 and right brace 12 of upper brace 10 each include rail 22 with closure attachment points 23, and connection section 19 with connecting hole 20 for connector 110. Closure attachment points 23 may be formed as slots 24 for receiving adjustable strap 110.

With particular reference to FIGS. 1A, 2B, 2, 3, 5A, & 5B, stoppable hinge section 14 includes stop receiver 15 with angular settings 120 for a range of permissible flexion 142 (and thus creating a range of impermissible flexion 143). Stop receiver 15 includes multiple stop detents 16 separated by angular spacing 17. Angular spacing 17 permits angular settings 120, including at least: least flexion setting 121, one or more intermediate flexion settings 122, and most flexion setting 123. Stop detents 16 are linear/slot-like depressions formed on each side of stop receiver 15, and extend inwardly from the edge approximately towards connecting hole 20 (approximately because the detents may be offset off-center by edge spacing 57 to accommodate interaction of stopping tab 90 and edge 55).

Lower brace 11 includes left brace 52 and right brace 51, with each of left and right braces 52, 51 including a supporting arm 77. Each supporting arm 67 itself includes proximal arm 68 and distal arm 69. Supporting arms 67 include side portions 70 for extending toward the bottom of the arm of patient 130, and connection portions 71 for connecting an arm on one side brace (left brace 52/right brace 51) to an arm on the opposing side brace (right brace 51/left brace 52). Side portions 70 and connection portions 71 are part of proximal arm 68 and distal arm 69.

With particular reference to FIGS. 3, 4A, & 4B, on one of left brace 52/right brace 51 (and as illustrated on FIG. 3, inverted left/right from left brace 11/right brace 12), connection portion 71 includes proximal arm 68 and distal arm 69 extending from rail 62, crosspiece 73 spaced from rail 62 and connecting proximal arm 68 and distal arm 69 transversely, and receiving slots 74 having mouths 75 formed in proximal arm 68 and distal arm 69 for opposed mating arms on the other of left brace 52/right brace 51. Mouths 75 permit access to receiving slots 74 within each of proximal arm 68 and distal arm 69 by space between flat wall 78 and toothed wall 79 having meshing teeth 80. Toothed walls 79 (and flat walls 78) are in opposing directions in proximal arm 68 and distal arm 69 and are both outboard to permit a compressed flexed position 86 (depicted by analogy to flexed position 46 in FIG. 4A) to remove ratchet mechanism 77 from locked position 88. Receiving slots 74 each include internal flat wall 78 longitudinal to the arm, opposing toothed wall 89 formed of meshing teeth 80, and mouth 75 on each arm exposing receiving slots 74. On the other of left brace 52/right brace 51, connection portion 71 includes proximal arm 68 and distal arm 69 extending from rail 62, each with flexible piece 85 having locking ends 83 (having teeth 84) facing opposing directions and outboard to permit a compressed flexed position 86 to remove ratchet mechanism 77 from locked position 88 or to back it off (i.e. loosen left brace 52/right brace 51). Flexible pieces 45 are spaced from rail 62 and include locking ends 83 with teeth 84 located distally on the arms. The spacing between side braces (left brace 52/right brace 51) of lower brace 50 are adjustable between connection portions 71 via ratchet mechanisms 77, which ratchets as distance is reduced (i.e. tightening left brace 52/right brace 51), but may be released by flexing one or more of flexible pieces 85. Thus, connection portions 71 are matable to one another to adjustably connect side braces (left brace 52/right brace 51). Supporting arms 67 have flexed position 86 and unflexed position 87, the latter causing the arms to be in locked position 88 with teeth 84 and meshing teeth 80 engaged. Flexed position 86 permits releasing ratchet mechanisms 77 formed by locking ends 83 and toothed walls 79 to allow increasing the spacing between left brace 52 and right brace 51 of lower brace 50 (i.e. loosen left brace 52/right brace 51) by disengaging teeth 84 and meshing teeth 80. Unflexed position 87 engages ratchet mechanisms 77 formed by locking ends 83 and toothed walls 79 to allow decreasing the spacing between left brace 52 and right brace 51 (i.e. tighten left brace 52/right brace 51) while preventing that spacing from increasing without departing unflexed position 87 and locked position 88; thus teeth 84 and meshing teeth 80 are engaged but permit decreasing spacing.

With particular reference to FIGS. 1A, 2B, 2, 3, & 5A, left brace 52 and right brace 51 of lower brace 50 each include rail 62 with closure attachment points 63, and connection section 59 with connecting hole 60 for connector 110. Closure attachment points 63 may be formed as slots 64 for receiving adjustable strap 100.

With particular reference to FIGS. 1A, 2B, 2, 3, 5A, & 5B, stoppable hinge section 54 includes edge 55 for interacting with stop 6 or stopping tab 90, with edge 55 spaced by edge spacing 57 from the centerline of connecting hole 60.

With particular reference to FIGS. 1A, 2B, 2, 3, & 5A, connector 110 rotatably joins upper brace 10 and lower brace 11. Connector 110 may include bolt 111, locking nut 111, and washer 113, where locking nut 111 and washer 113 hold bolt 111 in place through and rotatably joining connecting sections 19 via connecting holes 20 to connection section 59 via connecting holes 60. Connection section 19 of left brace 11 of upper brace 10 is thus rotatably connected to connection section 59 of left brace 52 of lower brace 50 and connection section 19 of right brace 12 of upper brace 10 is thus rotatably connected to connection section 59 of right brace 51 of lower brace 50, each about an axis defined by connector 110.

In addition, connector 110 holds stoppable hinge section 14 of upper brace 10 to be closely adjacent/touching stoppable hinge section 54 of lower brace 50 between bolt 111 and washer 113. Stoppable hinge section 14 is held in a rotatable and closely adjacent/touching relationship with stoppable hinge section 54 about an axis defined by connector 110. In so doing, relative rotation between stoppable hinge section 14 and stoppable hinge section 54 causes edge 55 to sweep across stop receiver 15 and past stop detents 16 except as stop 6 or stopping tab 90 prevents such rotation and sweep by being set into stoppable hinge 5 or stoppable hinge section 14.

With particular reference to FIGS. 1A, 2B, 2, 3, & 5A, brace system 1 also includes stopping tab 90, for setting the range of permissible flexion 142 and impermissible flexion 143. Stopping tab 90 includes slot end 92, opposing tab end 93, and slot 91 for interacting with stop detents 16 (of stoppable hinge section 14 on upper brace 10) and also interacts with edge 55 (of stoppable hinge section 54 on lower brace 50). Slot 91 is configured to fit over any one of stop detents 16 by inserting stopping tab 90 slot end 92 inwardly first, thus leaving tab end 93 extending outwardly from stop receiver 15. Stopping tab 90 may be removed by pulling tab end 93 extending outwardly from stop receiver 15 to slide slot 91 from stop detent 16. Because stoppable hinge section 14 and stoppable hinge section 54 are held closely adjacent/touching, that position also interferes with edge 55 sweeping across stop receiver 15 or past stop detents 16, by causing edge 55 to reach positive rotational stop 141 at stopping tab 90. Choosing a stop detent 16 in which to fit stopping tab 90 to involves choosing one of angular settings 120: least flexion setting 121, one or more intermediate flexion settings 122, and most flexion setting 123. Preferably a matched pair of stopping tabs 90 are inserted onto matching stop detents 16 on left brace 11 and right brace 12 to create a more solid stop and to avoid twist of brace system 1. Stop receiver 15, by having angular settings 120 caused by stopping tabs 90 and stop detents 16, permits brace system 1 to prevent impermissible elbow flexion 143 while permitting permitted elbow flexion 142.

With particular reference to FIGS. 1A, 2B, 2, & 5A, adjustable strap 110 includes buckle 101 having slot 102 for accepting free end 104 of adjustable strap 110, having free end 104 to loop around to engage adjustable strap 110 via portions of hook-and-loop fabric 105. This allows adjustments to fit upper brace 10 and lower brace 50 about upper arm 132 and lower arm 133 of patient 130.

Figure 5A:
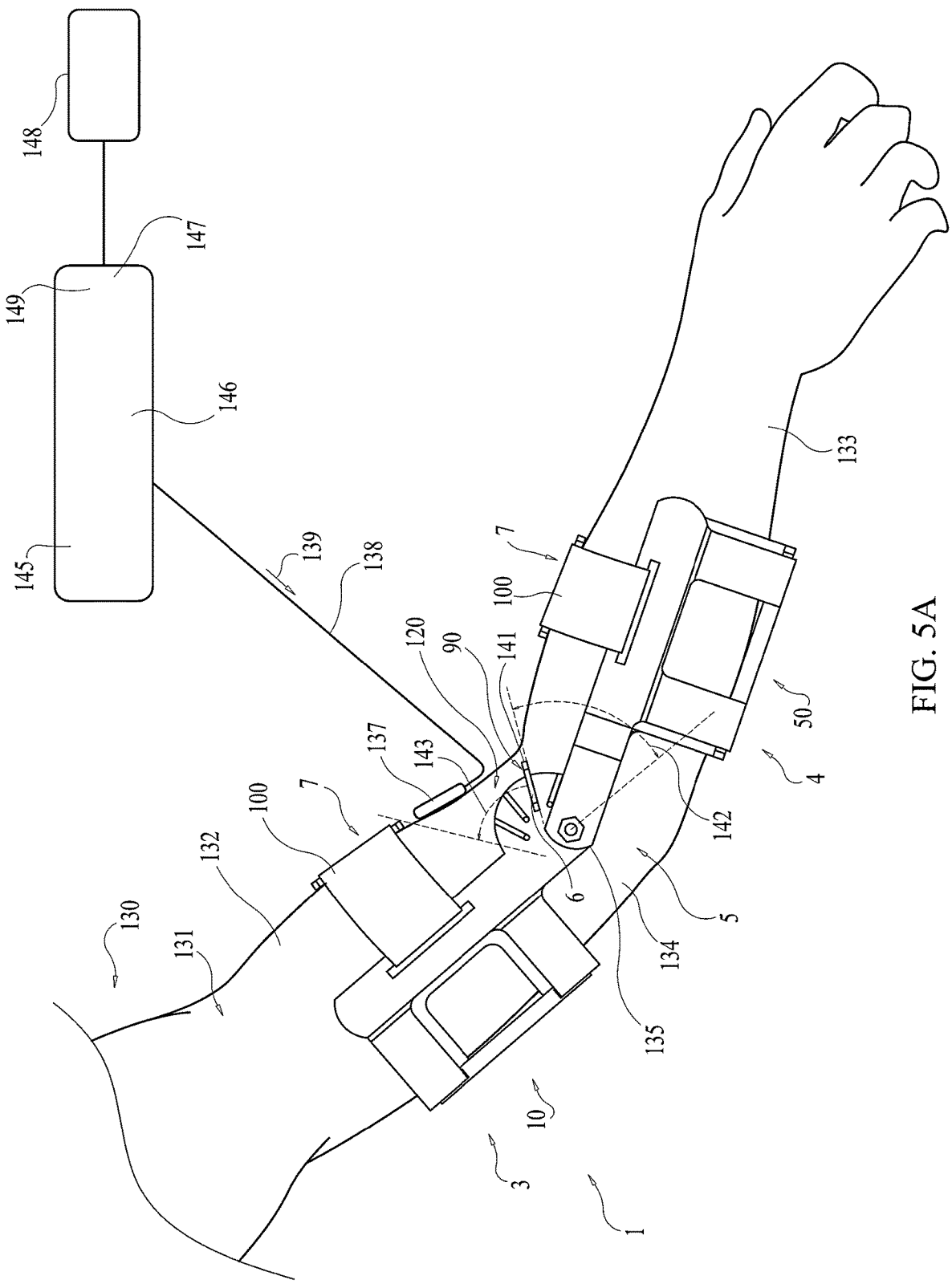
FIGS. 5A & 5B show right side views of an embodiment of the present invention in a first and second configuration.
Figure 5B:
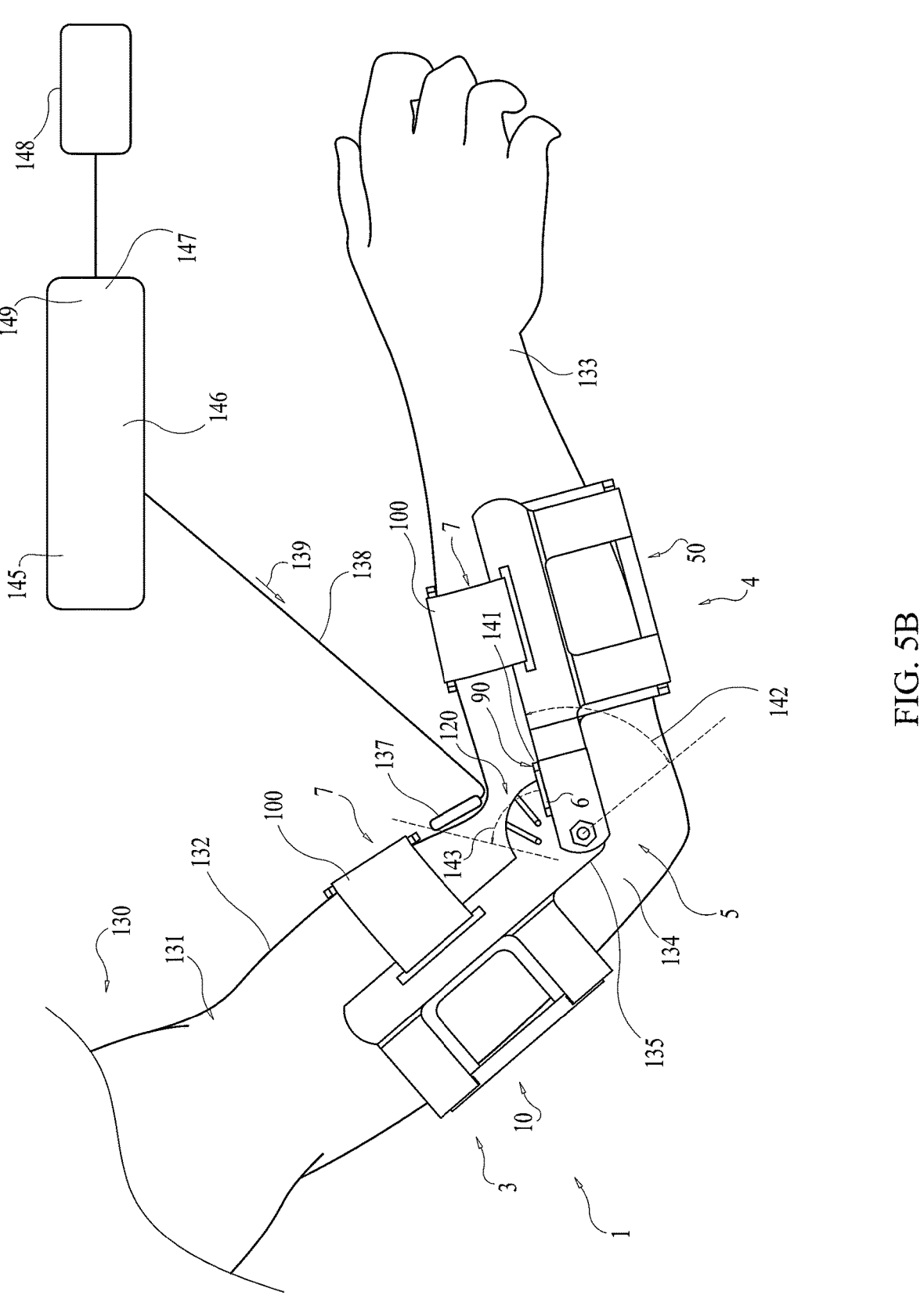

With particular reference to FIGS. 5A & 5B, an IV is in place at AC elbow intravenous site 137 on patient 130, near elbow 134. Intravenous site 137 is attached via IV line 138 to pump 145 (which itself has a source of IV fluid). Pump 145 pumps fluid flow 139 from pump 145, through IV line 138, and into patient 130 via elbow intravenous site 137. Stopping tab 90 is set and at one of intermediate flexion setting 122, so as to create permissible flexion 142 to that setting and not beyond into impermissible flexion 143. Alarm system 147 is attached to pump 145 and has sensor 146 and alarm 148 controlled by input to sensor 146. Sensor 146 and alarm system 147 can be set to alert/alarm when sensor 146 detects that fluid flow 139 (such as in pump 145) has stopped (e.g. gone to zero flow) or dropped below a preset alarm flow 149. Or alarm system 147 may be omitted by relying upon positive rotational stop 141 caused by brace system 1.

Figure 6A:
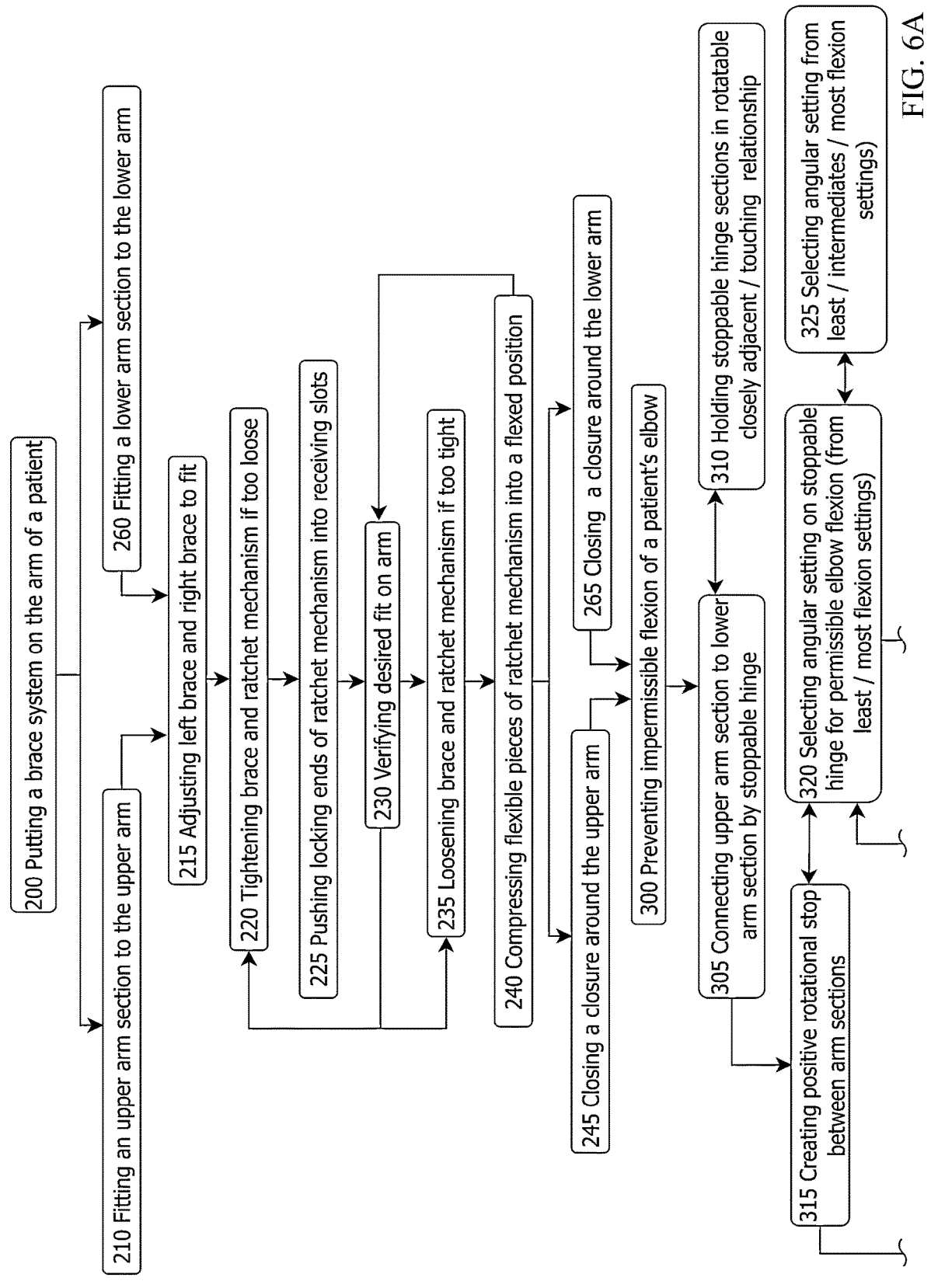
FIGS. 6A-6B show an embodiment of a process of the present invention.
Figure 6B:
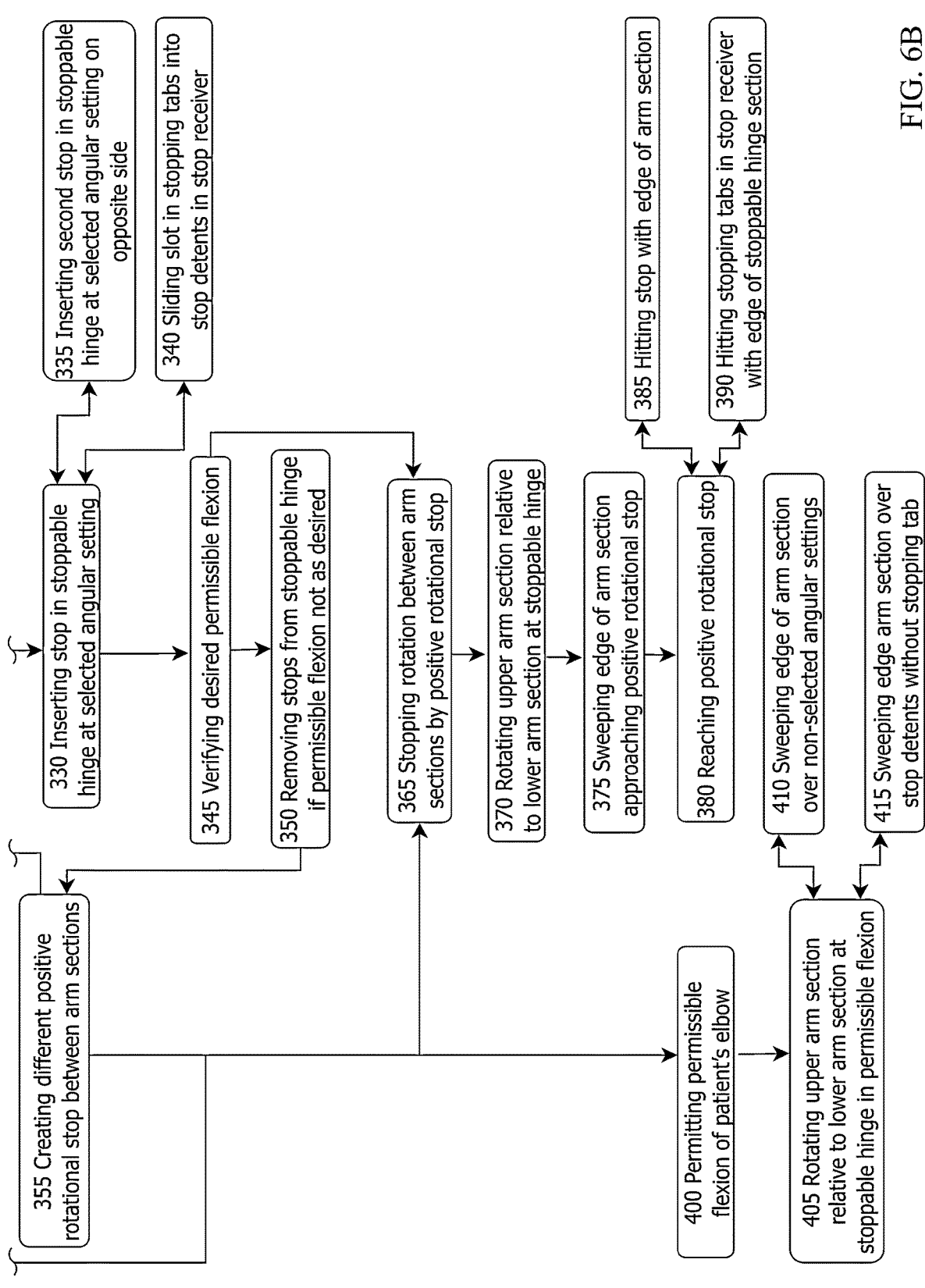

With particular reference to FIG. 6, a method of preventing impermissible elbow flexion and permitting permissible elbow flexion includes:

200 Putting a brace system on the arm of a patient.
210 Fitting an upper arm section of the brace system to the patient's upper arm.
215 Adjusting the left brace and right brace to fit the arm.
220 Tightening brace and ratchet mechanism if too loose.
225 Pushing locking ends of a ratchet mechanism into receiving slots with toothed walls.
230 Verifying desired fit on arm.
235 Loosening brace and ratchet mechanism if too tight.
240 Compressing flexible pieces of ratchet mechanism into a flexed position to loosen ratchet mechanism.
230 Verifying desired fit on arm.
245 Closing a closure around the upper arm to connect the brace system to the upper arm.
260 Fitting a lower arm section of a brace system to the patient's lower arm.
215 Adjusting the left brace and right brace to fit the arm.
220 Tightening brace and ratchet mechanism if too loose.
225 Pushing locking ends of a ratchet mechanism into receiving slots with toothed walls.
230 Verifying desired fit on arm.

235 Loosening brace and ratchet mechanism if too tight.
240 Compressing flexible pieces of ratchet mechanism into a flexed position to loosen ratchet mechanism.
230 Verifying desired fit on arm.
265 Closing a closure around the lower arm to connect the brace system to the lower arm.
300 Preventing impermissible flexion of a patient's elbow.
305 Connecting the upper arm section to the lower arm section by a stoppable hinge.
310 Holding a stoppable hinge section of the upper arm section in a rotatable and closely adjacent/touching relationship with a stoppable hinge section of the lower arm section.
315 Creating a positive rotational stop between the upper arm section and the lower arm section.
320 Selecting an angular setting on the stoppable hinge for permissible elbow flexion, from among a least flexion setting and a most flexion setting.
325 Selecting an angular setting for permissible elbow flexion, from among a least flexion setting, one or more intermediate flexion settings, and a most flexion setting.
330 Inserting a stop in the stoppable hinge at the selected angular setting for permissible elbow flexion.
335 Inserting a second stop in the stoppable hinge at the selected angular setting on the opposite side of the stoppable hinge.
340 Sliding a slot in stopping tabs into stop detents in a stop receiver on one of the upper brace or lower brace at the selected angular setting.
345 Verifying accurate desired permissible flexion.
350 Removing the stops from the stoppable hinge if permissible flexion is not as desired.
355 Creating a different positive rotational stop between the upper arm section and the lower arm section.
320 Selecting an angular setting on the stoppable hinge for permissible elbow flexion, from among a least flexion setting and a most flexion setting.
325 Selecting an angular setting for permissible elbow flexion, from among a least flexion setting, one or more intermediate flexion settings, and a most flexion setting.
330 Inserting a stop in the stoppable hinge at the selected angular setting for permissible elbow flexion.
335 Inserting a second stop in the stoppable hinge at the selected angular setting on the opposite side of the stoppable hinge.
340 Sliding a slot in stopping tabs into stop detents in a stop receiver on one of the upper brace or lower brace at the selected angular setting.
345 Verifying accurate desired permissible flexion.
365 Stopping rotation between the upper arm section and the lower arm section by the positive rotational stop.
370 Rotating the upper arm section relative to the lower arm section at the stoppable hinge.
375 Sweeping an edge of one the upper arm section and the lower arm section approaching to the positive rotational stop.
380 Reaching a positive rotational stop.
385 Hitting the stop with an edge of one of the upper arm section and the lower arm section.
390 Hitting stopping tabs in the stop receiver with the edge of a stoppable hinge section.
400 Permitting permissible flexion of a patient's elbow.

405 Rotating the upper arm section relative to the lower arm section at the stoppable hinge in permissible flexion.

410 Sweeping an edge of one of the upper arm section and the lower arm section over non-selected angular settings.

415 Sweeping an edge of one of the upper arm section and the lower arm section over stop detents without a stopping tab.

The invention claimed is:

1. An arm brace system configured to adjustably permit flexion of a patient's elbow, comprising: an upper arm section and a lower arm section; a stoppable hinge connecting the upper arm section and the lower arm section; the stoppable hinge comprising at least one stop; and a plurality of angular settings; a plurality of stop detents, said stop detents separated by angular spacing; said angular spacing permitting said plurality of angular settings; the plurality of stop detents each comprising a slot-shaped depression in the stoppable hinge; the at least one stop comprising at least one removeable stopping tab, the stopping tab having a slot formed therein, a slot end, and an opposing tab end; and said slot inserted into the slot-shaped depression of one of said plurality of stop detents.

2. The arm brace system of claim 1, further comprising: one of said upper arm section and said lower arm section comprising a stop receiver; the other of said upper arm section and said lower arm section comprising an edge; said at least one stop preventing rotation of the edge across the stop receiver at one of said plurality of angular settings.

3. The arm brace system of claim 2, further comprising:
a first stoppable hinge section on said upper arm section;
a second stoppable hinge section on said upper arm section; and
a connector rotatably joining the stoppable hinge sections;
one of said stoppable hinge sections comprising the stop receiver; and
the other of said stoppable hinge sections comprising the edge.

4. The arm brace system of claim 1, said upper arm section comprising a first brace and a second brace; said first brace comprising a connection portion; said second brace comprising a connection portion matable with the connection portion of said first brace; said connection portions connected to one another by a ratchet mechanism.

5. The arm brace system of claim 4:
the connection portion of said first brace comprising locking ends comprising teeth; and
the connection portion of said second brace comprising a slot having a toothed wall.

6. The arm brace system of claim 1, the plurality of angular settings comprising at least a least flexion setting, an intermediate flexion setting, and a most flexion setting.

7. The arm brace system of claim 1: the stoppable hinge comprising at least one stop receiver; said plurality of stop detents formed in the at least one stop receiver.

8. The arm brace system of claim 1, said upper arm section and said lower arm section each comprising a left brace and a right brace; and the stoppable hinge comprising at least two stop receivers.

9. The arm brace system of claim 1: each of said upper arm section and said lower arm section comprising left and right side braces; said left side braces connected to said right side braces by a ratchet mechanism.

10. The arm brace system of claim 1, further comprising:
a positive rotational stop; the positive rotational stop formed by said at least one stop inserted into said stoppable hinge; said positive rotational stop permitting permissible elbow flexion and preventing impermissible elbow flexion.

11. A method of adjustably permitting flexion of a patient's elbow, comprising: connecting an upper arm section and a lower arm section with a stoppable hinge; the stoppable hinge comprising at least one stop; and a plurality of angular settings;
preventing rotation of an edge on one of said upper arm section and said lower arm section across a stop receiver on the other of said upper arm section and said lower arm section; said preventing step comprising the at least one stop being at one of said plurality of angular settings; a removeable stopping tab having a slot formed therein, a slot end, and an opposing tab end; said preventing step further comprising inserting the stopping tab into one of a plurality of stop detents separated by angular spacing; the plurality of stop detents each comprising a slot-shaped depression in the stop receiver; and the inserting step comprising sliding the slot of the stopping tab slot end first into the slot-shaped depression.

12. The method of claim 11, further comprising: permitting permissible elbow flexion; and preventing impermissible elbow flexion.

13. The method of claim 12, further comprising:
selecting one of the plurality of angular settings to define a range of permissible elbow flexion.

14. The method of claim 11, further comprising: adjusting the spacing between left and right side braces of each of said upper arm section and said lower arm section; said adjusting step comprising using a ratchet mechanism.

15. The method of claim 14:
said using step comprising inserting locking ends comprising teeth into a slot having a toothed wall.

16. The method of claim 11, further comprising: selecting one of said plurality of angular settings; and hitting the at least one stop with an edge of one of the upper arm section and the lower arm section.

17. The method of claim 16, further comprising:
the at least one stop being at said selected angular setting.

18. The method of claim 16, further comprising:
sweeping the edge over at least one non-selected angular setting.

19. The method of claim 11, further comprising: selecting an angular setting for permissible elbow flexion, from among a least flexion setting, one or more intermediate flexion settings, and a most flexion setting.

20. The method of claim 11, further comprising:
removing the removeable stopping tab from the hinge.

21. A method of limiting permitted flexion of a patient's elbow comprising: selecting one of a plurality of angular settings on a hinged arm brace system to define a range of permissible elbow flexion; the selecting step further comprising inserting a stop in a hinge at the selected angular setting; rotating an upper arm section of said arm brace system relative to a lower arm section of said arm brace system; and reaching a positive rotational stop on said arm brace system; the stop being removeable and comprising a slot formed therein, and a slot end; the hinge comprising a plurality of stop detents; the plurality of stop detents each comprising a slot-shaped depression in the hinge; and the inserting step further comprising sliding the slot of the stop slot end first into the slot-shaped depression.

22. The method of claim 21: the rotating step further comprising sweeping over at least one non-selected angular setting.

23. The method of claim 21: the reaching step further comprising hitting at least one stop with an edge of one of the upper arm section and the lower arm section.

24. The method of claim 21, further comprising: fitting the arm brace system by using a ratchet mechanism to adjust the spacing between left and right side braces of each of said upper arm section and said lower arm section.

\* \* \* \* \*